(12) United States Patent
Hadba et al.

(10) Patent No.: US 9,636,015 B2
(45) Date of Patent: May 2, 2017

(54) COLON POLYP STAGING METHODS

(75) Inventors: Ahmad R. Hadba, Middlefield, CT (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 999 days.

(21) Appl. No.: 12/527,445

(22) PCT Filed: Apr. 11, 2008

(86) PCT No.: PCT/US2008/059985
§ 371 (c)(1),
(2), (4) Date: Aug. 17, 2009

(87) PCT Pub. No.: WO2008/130866
PCT Pub. Date: Oct. 30, 2008

(65) Prior Publication Data
US 2010/0087740 A1    Apr. 8, 2010

Related U.S. Application Data

(60) Provisional application No. 60/923,901, filed on Apr. 17, 2007.

(51) Int. Cl.
| | | |
|---|---|---|
| A61B 1/04 | (2006.01) | |
| A61B 5/103 | (2006.01) | |
| A61B 5/00 | (2006.01) | |
| A61B 1/313 | (2006.01) | |
| A61B 17/34 | (2006.01) | |
| A61B 17/00 | (2006.01) | |
| A61B 90/00 | (2016.01) | |

(52) U.S. Cl.
CPC .............. *A61B 5/00* (2013.01); *A61B 1/313* (2013.01); *A61B 5/411* (2013.01); *A61B 17/3478* (2013.01); *A61B 2017/00022* (2013.01); *A61B 2017/00057* (2013.01); *A61B 2017/00269* (2013.01); *A61B 2090/064* (2016.02)

(58) Field of Classification Search
None
See application file for complete search history.

(56) References Cited

U.S. PATENT DOCUMENTS

| | | | | |
|---|---|---|---|---|
| 4,411,257 A | | 10/1983 | Machida | |
| 5,634,463 A | * | 6/1997 | Hayafuji | 600/405 |
| 5,741,271 A | * | 4/1998 | Nakao et al. | 606/114 |
| 5,846,248 A | * | 12/1998 | Chu et al. | 606/114 |
| 5,976,073 A | * | 11/1999 | Ouchi | 600/129 |
| 6,010,512 A | * | 1/2000 | Chu et al. | 606/113 |
| 6,086,542 A | * | 7/2000 | Glowa et al. | 600/561 |
| 6,319,260 B1 | * | 11/2001 | Yamamoto | 606/113 |

(Continued)

FOREIGN PATENT DOCUMENTS

WO    WO 2004/047651 A2    6/2004

OTHER PUBLICATIONS

International Search Report for PCT/US08/059985 date of completion is Sep. 24, 2008 (2 pages).

(Continued)

*Primary Examiner* — Katherine Fernandez
*Assistant Examiner* — Farshad Negarestan

(57) ABSTRACT

Systems and methods are provided for examination and removal of polyps. Using methods and systems of the present disclosure, one can determine whether a polyp is benign or cancerous in situ.

5 Claims, 9 Drawing Sheets

(56) References Cited

U.S. PATENT DOCUMENTS

| | | | |
|---|---|---|---|
| 6,488,659 B1 | 12/2002 | Rosenman | |
| 6,537,211 B1 | 3/2003 | Wang et al. | |
| 6,596,257 B2 | 7/2003 | Bryan | |
| 7,033,373 B2* | 4/2006 | de la Torre et al. | 606/191 |
| 2006/0069310 A1* | 3/2006 | Couvillon, Jr. | 600/148 |
| 2006/0070631 A1 | 4/2006 | Scopton et al. | |

OTHER PUBLICATIONS

European Search Report for EP 08745570.5-1526 date of completion is Nov. 21, 2011 (4 pages).
Uno Y. et al. "The non-lifting sign of invasive colon cancer" Gastrointestinal Endoscopy, Elsevier, NL, vol. 40, No. 4, Jul. 1, 1994, pp. 485-489.
Yamamoto H. et al.: "A Novel Method of Endoscopic Mucosal Resection Using Sodium Hyaluronate", Gastronintestinal Endlscopy, Elsevier, NL, vol. 50, No. 2, Aug. 1, 1999, pp. 251-256.
Asaki S. et al.: "Diagnosis of submucosal tumors by injecting a water soluble contrast medium: basic research and imaging of tumors." The Tohoku Journal of Experimental Medicine Oct. 1982 LNKD—Pubmed: 7179270 vol. 138, No. 2, Oct. 1982, pp. 121-130.

\* cited by examiner

COLON POLYP STAGING METHODS

CROSS-REFERENCE TO RELATED APPLICATIONS

This application is a National Stage Application of PCT/US2008/059985 under 35 USC §371 (a), which claims priority of U.S. Provisional Patent Application Ser. No. 60/923,901 filed Apr. 17, 2007, the disclosures of each of the above-identified applications are hereby incorporated by reference in their entirety.

TECHNICAL FIELD

The present disclosure relates to methods for endoscopic polypectomy. The methods, in embodiments, include the use of sensors and materials which permit excellent visualization of a polyp during an endoscopic procedure and, where necessary, the removal of such a polyp.

BACKGROUND

A polyp is generally a growth that projects from a membrane in the body. The shape of a polyp is often described as pedunculated or sessile. Pedunculated polyps grow on stalks, while sessile polyps may have broad bases and a flat appearance. Often, polyps form on mucous membranes such as those lining the colon, bladder, uterus, cervix, vocal cords, and/or nasal passage and protrude into a body cavity. Polyps are problematic in that they may block a passage, and/or may become cancerous.

Endoscopic polypectomy procedures are effective in removing pedunculated polyps; however, sessile polyps may be problematic. For example, because of their flat, diffuse appearance, sessile polyps may be difficult to snare and excise with electrocautery. To facilitate excision of some polyps, saline or other materials may be injected into the submucosa of a polyp to create an artificial cushion that raises the polyp.

Means for introducing injection solutions into a polyp include endoscopic methods which may, in embodiments, include the use of catheters and/or cannulas. As is within the purview of those skilled in the art, cannulas may include tubular, flexible, surgical instruments for withdrawing fluids from (or introducing fluids into) a cavity of the body. Cannulas may have a single lumen or may have multiple lumens; multi-lumen cannulas, including dual lumen cannulas, are also within the purview of those skilled in the art.

Various configurations for multi-lumen catheters and/or cannulas are also known. For example, U.S. Pat. No. 4,385,631 discloses a hemodialysis catheter having two circular lumens arranged side by side. U.S. Pat. No. 4,099,528 discloses a coaxial double lumen cannula and U.S. Pat. No. 4,493,696 describes a coaxial double lumen catheter.

There remains room for improvement in methods for performing endoscopic polypectomy procedures, and especially to enhance the ability of a physician to determine whether or not a polyp is cancerous during the polypectomy procedure.

SUMMARY

Systems and methods are provided for examination and removal of polyps. In embodiments, a method of the present disclosure may include introducing at least one media into tissue comprising submucosa of a polyp, measuring a response to an external stimuli in the tissue, and deducing a state of health of the tissue depending on the response to external stimuli.

Media which may be utilized include saline, thermally responsive polymers, thermoreversible polymers, combinations thereof, and the like.

In embodiments, the external stimuli may include palpation and measuring the response may be performed with a device such as pressure sensors, force sensors, cameras, surface geometry scanning devices, and combinations thereof. In other embodiments, the external stimuli may include an air puff and measuring the response may be performed with a device such as a tonometer. In yet other embodiments, the external stimuli may include a light source and measuring the response may be performed with a device such as a camera, which can be placed above or below the polyp.

In embodiments, a system of the present disclosure may include a cannula for introducing at least one media into tissue including the submucosa of a polyp, at least one sensor for determining changes in the tissue, and display means for displaying data from the sensor to an end-user.

In embodiments, the sensor utilized to determine changes in tissue may be an air tonometer which, in turn, may include a nozzle for blowing air onto a polyp, a sensor capable of measuring the pressure of the media injected below the mucosal layer, and a CPU.

In embodiments, the cannula may be utilized to introduce into the polyp additional items such as medicines, drugs, blood, medical devices, guide wires, polypectomy snares, electrocautery devices, needles, optical fibers, fiber optic imaging devices, fiber optic diagnostic probes, and combinations thereof.

In embodiments, the methods and systems of the present disclosure may be utilized to determine whether or not a polyp is cancerous, and may permit such a determination to occur in real time.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
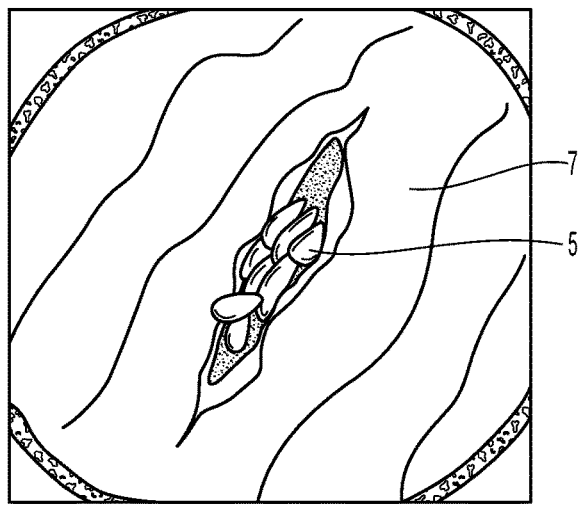
FIG. 1A is a schematic illustrations of a sessile villous adenoma near the cecum of a 65 year old man.

The present disclosure provides systems and methods for visualizing polyps during a polypectomy procedure. In embodiments, the present disclosure provides systems and methods for determining the cancerous nature of a polyp during a polypectomy procedure, without having to wait for biopsy or similar test results to determine whether or not a polyp is benign or cancerous. Such early detection may be desirable in cancer treatment.

Thus, in accordance with the present disclosure, methods and apparatus are provided to permit a physician to determine, during a polypectomy procedure, whether or not a polyp is cancerous. For example, a physician may determine the cancerous nature of a polyp, including its tumor stage, by the biomechanics exhibited by the polyp as it rises from the mucosal wall. For example, larger tumors or those that have spread into the wall of the colon may be stiffer or rise from the mucosal surface to a lesser degree than smaller, non-cancerous tumors.

In embodiments, a method of the present disclosure may include injecting a fluid or similar media into the mucosal layer under a polyp. Any media capable of raising the mucosal layer may be utilized. In embodiments, saline may be utilized to raise the mucosal layer and permit analysis of the surface of the mucosal layer as well as any polyps thereon. In other embodiments, thermally responsive polymers may be utilized in combination with saline, or instead of saline, to raise the mucosal layer and permit analysis of the surface of the mucosal layer as well as any polyps thereon.

Thermally responsive polymers which may be utilized in accordance with the present disclosure may include one or more polymeric substances that undergo a change in viscosity with a change in temperature, for example, warming. In embodiments, the thermally responsive polymers may be in a solution including at least one solvent, with other excipients and/or ingredients to form a composition of the present disclosure. In embodiments, additional excipients and/or ingredients may be added to facilitate usage of the compositions and adjust their viscosity, for example, during a polypectomy procedure. As used herein, "viscosity" refers to a measure of the resistance of a fluid to deform under shear stress and is used herein to describe a fluid's internal resistance to flow. For example, water has a relatively lower viscosity, while substances like vegetable oil or honey have a higher viscosity.

Suitable polymers for use as the thermally responsive polymers in accordance with the present disclosure include, but are not limited to, thermoreversible polymers, poloxamers, polyoxyalkylene block copolymers, alkyl cellulose, hydroxyalkyl cellulose, cellulosic ethers, poly(n-isopropylacrylamide), PEG triblock copolymers of L-lactide, glycolide, polyglycolides (PGA), and copolymers of glycolides such as glycolide/lactide copolymers (PGA/PLLA) or glycolide/trimethylene carbonate copolymers (PGA/TMC), D, L-lactide, L-polylactides (PLA) and stereocopolymers of polylactides such as poly-L-lactide (PLLA), poly-DL-lactide copolymers and L-lactide/DL-lactide copolymers, ε-caprolactone, trimethylene carbonate (TMC), PEG-grafted chitosan, pectin-chitosan mixtures, methyl cellulose, gelatin, and combinations thereof. Other suitable materials which may be utilized to form the thermally responsive polymers include glycerin, dextrose, hyaluronic acid, hydroxypropyl cellulose, hydroxyethyl cellulose, hydroxylpropyl methyl cellulose (HPMC), combinations thereof, and the like.

The polymer may be dissolved in a solvent at a concentration of from about 10% to about 70% by weight of the solution in embodiments from about 20% to about 60% by weight of the solution; thus the solvent may be present in an amount from about 90% to about 30% by weight of the solution, in embodiments from about 80% to about 40% by weight of the solution. In embodiments, the polymer concentration may be such that the composition in accordance with the present disclosure is in a low viscosity state at a pre-treatment temperature and a higher viscosity state at a treatment temperature that is higher than the pre-treatment temperature. The polymer concentration may also be such that the composition in accordance with the present disclosure is in a highly viscous shear thinning state at a pre-treatment temperature and a higher viscosity state at a treatment temperature that is higher than the pre-treatment temperature.

As used herein, "pre-treatment temperature" refers to the temperature of the thermally responsive polymers prior to being applied in the body of a patient, for example the submucosa of a polyp. The pre-treatment temperature may be room temperature, for example from about 23° C. to about 25° C., or any temperature below the treatment temperature. As used herein, "treatment temperature" refers generally to the temperature of the thermally responsive polymers after being applied to the body, for example the submucosa of a polyp. The treatment temperature may be the normal body temperature for a human, for example about 37° C., or any temperature found within the body, including, for example, the temperature of a polyp to be treated. While the healthy human body can maintain a fairly consistent body temperature of about 37° C., the temperature may vary by about ±2° C., with factors that may affect treatment temperature including the age of the individual, the time of day, or the part of the body in which the temperature is being measured at, and the like.

In embodiments, polyoxyalkylene polymers, including polymeric surfactants available under the tradename PLURONICS, may be utilized as the thermally responsive polymer. These polymers are commercially available from BASF Corporation. Such polymers are closely related block copolymers classified as polyoxypropylene-polyoxyethylene condensates that terminate in primary hydroxyl groups, and may be formed by the condensation of propylene oxide into a propylene glycol nucleus followed by the condensation of ethylene oxide onto both ends of the polyoxypropylene base. The polyoxyethylene hydrophilic groups on the ends of the base pre-polymer may be controlled in length so that they account for from about 10% to about 80% by weight of the final polymer. The PLURONIC polymer series of products may be represented empirically by the formula: $HO(C_2H_4O)_a(C_3H_6O)_b(C_2H_4O)_cH$, where a and c are statistically equal.

The thermally responsive polymer may include a mixture of other polyoxyalkylene polymers and/or various PLURONIC polymers. In some embodiments, a first block copolymer and a second block copolymer may be utilized. For example, a first block copolymer of ethylene oxide and propylene oxide, such as PLURONIC F-127, may be mixed with a second block copolymer of ethylene oxide and propylene oxide, such as PLURONIC F-68, in a solution. In some embodiments, the first block copolymer may be present in amounts of from about 10% to about 50% by weight of the solution. The first block copolymer such as PLURONIC F-127 may have a solubility in water at about 4° C. of greater than about 10%. (As concentration increases, the gelation temperature decreases.) In other embodiments, the first block copolymer may be present in amounts of from about 15% to about 30% by weight of the solution.

The second block copolymer, in embodiments F-68, may be present in an amount of from about 5% to about 50% by weight of the solution. The second block copolymer, such as, for example, PLURONIC F-68, may have a solubility in water at about 4° C. of greater than about 10%. In embodiments, the second block copolymer may be present in an amount of from about 5% to about 25% by weight of the solution.

The first block copolymer, the second block copolymer, or both, may have a molecular weight of from about 7680 to about 14600 g/mol. In embodiments, the first block copolymer may have a molecular weight of from about 7680 to about 9510 g/mol, while the second block copolymer may have a molecular weight of from about 9840 to about 14600 g/mol.

In some embodiments, suitable media capable of raising the mucosal layer in methods of the present disclosure may include a solvent, from about 10% to about 50% by weight of a first block copolymer of ethylene oxide and propylene oxide, and from about 5% to about 50% by weight of a second block copolymer of ethylene oxide and propylene oxide. Thus, suitable compositions may include an aqueous solvent, and about 15% to about 50% by weight of a thermally responsive polymer admixture.

In embodiments, the first and second block copolymers may be thermoreversible. Suitable thermoreversible polymers may be added to the compositions in accordance with the present disclosure in an amount sufficient to reversibly change the viscosity thereof in response to changes in temperature. For example, a composition having a high viscosity at 37° C. may thin and have a low viscosity at 25° C., yet thicken again upon application of heat. Thus, such a composition may be a liquid at about 25° C. and a gel at a treatment temperature of about 37° C. In embodiments, thermoreversible polymers may be added to an aqueous solution incorporating a stable combination or admixture of one or more thermoreversible polymers and/or thermally responsive polymers in amounts sufficient to effectively produce reversible gelation at predetermined temperatures. As used herein reversible gelation refers to the increase and/or decrease in the viscosity of a composition due to a variation in temperature, where the composition becomes a gel or gel-like at one temperature, and a liquid at another lower temperature. Non-limiting examples of suitable thermoreversible polymers for use herein include alkyl celluloses, hydroxyalkyl celluloses, cellulosic ethers, PLURONIC® polymers and TETRONIC® polymers, and combinations thereof. In embodiments, thermoreversible polymers may be added in an amount of from about 10% to about 50% by weight of the composition of the present disclosure.

In embodiments, media capable of raising the mucosal layer utilized in methods in accordance with the present disclosure may include hyaluronic acid and/or derivatives thereof, such as sodium hyaluronic acid. In other embodiments, the media capable of raising the mucosal layer utilized in methods in accordance with the present disclosure may be devoid of hyaluronic acid and/or derivatives thereof such as sodium hyaluronic acid, or hyaluronic acid or derivatives thereof combined with any other chemical.

In embodiments, thermally responsive polymers utilized in methods in accordance with the present disclosure may transition from a liquid state to a gel or gel-like state at a temperature of from about 5° C. to about 40° C., in embodiments at a temperature of from about 15° C. to about 37° C., and in other embodiments at a temperature of from about 25° C. to about 35° C. In embodiments, the transition temperature can be modified by including polymers such as PLURONIC F-68.

Additionally, additives may be utilized to adjust the temperature at which the thermally responsive polymers form a semi-solid, sometimes referred to herein as a gel. Any additive within the purview of those skilled in the art may be utilized. The additives may be hydrophilic or hydrophobic. In embodiments, suitable hydrophilic additives include polyalkylene oxides including polyethylene glycols (PEG) of varying molecular weights such as PEG 8000, PEG 10000 and the like, n-sodium octyl sulfate, n-sodium decyl sulfate, n-dodecyl sulfate, n-hexadecyl sulfate, n-octadecyl sulfate, combinations thereof, and the like. Suitable other additives include, but are not limited to, salts such as NaCl, $Na_2SO_4$, $CaCl_2$, dyes such as methylene blue and isosulfan blue, antifoam agents, bioactive agents, combinations thereof, and the like. For example, in some embodiments SURFYNOL® MD-20, a non-silicone solvent-free liquid defoamer from Air Products and Chemicals, Inc. (Allentown, Pa.), may be added to adjust the gel temperature of the thermally responsive polymers.

In yet other embodiments, surfactants may be added to thermally responsive polymers to adjust the gel temperature. Suitable surfactants are within the purview of those skilled in the art and include, for example, sorbitan esters, polyolefin based surfactants, ethoxylates, combinations thereof, and the like. In some embodiments, commercially available surfactants such as TRITON® 100 and TRITON® 114 (nonionic surfactants from Sigma-Aldrich); TWEEN surfactants, SPAN surfactants, combinations thereof, and the like, may be utilized. Suitable TWEEN and SPAN surfactants include, but are not limited to, monolaureate (TWEEN 20, TWEEN 21, SPAN 20), monopalmitate (TWEEN 40, SPAN 40), monostearate (TWEEN 60, TWEEN 61, SPAN 60), tristearate (TWEEN 65, SPAN 65), monooleate (TWEEN 80, TWEEN 81, SPAN 80) and trioleate (TWEEN 85, SPAN 85), and the like.

Where utilized, the amount of such additives utilized to adjust the gel temperature of a thermally responsive polymer may vary from about 0.01% by weight to about 4% by weight of the composition, in embodiments from about 0.1% by weight to about 2.5% by weight of the composition, in embodiments from about 1% by weight to about 2.25% by weight of the composition, in other embodiments from about 1.5% by weight to about 2% by weight of the composition.

By adjusting the concentration of the copolymers and any additives, liquid to semi-solid transition temperatures between pre-treatment temperature and treatment temperature can be achieved. For example, the concentration of the thermally responsive polymers and the use of additives can be adjusted to provide compositions that are a liquid at a pre-treatment temperature, and a gel at treatment temperature. In embodiments, the liquid-gel transition temperature may be from about 5° C. to about 65° C. In some embodiments, the constituents can be selected in predetermined amounts to produce high viscosity shear thinning gel compositions. Such high viscosity shear thinning compositions may be suitable for injection in a high viscosity state such as a gel. In embodiments, the thermally responsive polymers at 25° C. have a viscosity of from about 50 centipoise to about 200,000 centipoise.

In shear thinning embodiments, thermally responsive polymers may transition from a semi solid and/or gel state to a more viscous semi-solid and/or gel state at a temperature from about 5° C. to about 50° C., in embodiments at a temperature from about 15° C. to about 40° C., and in some embodiments at a temperature from about 30° C. to about 37° C. As thermally responsive polymers may be used in the human body, in embodiments it may be desirable for the thermally responsive polymers to gel at a temperature close to human body temperature, which is about 37° C.

The solvent utilized with thermally responsive polymers may be water, saline, or any pharmaceutically acceptable solvent in amounts sufficient to solubilize the ingredients of the composition. For example, a non-limiting example of a suitable solvent includes an aqueous solution such as saline, resuspension buffer such as a phosphate buffered saline, or a buffer suitable for injection into a patient. Non-limiting examples of buffers suitable for injection into a patient include a pharmaceutically acceptable carrier such as a solution that does not cause allergic or other adverse reaction with the patient upon injection. The solvent may be present in an amount of from about 30% to about 90% by weight of the total composition. In embodiments, the concentration of water in the composition can be from about 30% to about 90% by weight of the composition, and/or from about 40% to about 80% by weight of the composition. The water used in forming the aqueous solution may be purified, as by distillation, filtration, ion-exchange, and the like.

Other excipients can be added to the compositions introduced into the submucosa and/or polyps in amounts sufficient to promote the removal of one or more polyps. For example, a dye may be added to the compositions to help the surgeon see the polyp better during the removal process. Non-limiting examples of suitable dyes include methylene blue, isosulfan blue, and combinations thereof. Dyes may be added in an amount of about 0.1% to about 2% by weight of the total composition.

Active ingredients can be added to these compositions in amounts sufficient to benefit the patient and the procedure for which the composition is provided, in embodiments a polypectomy procedure. While the amount of active agent used will depend on a number of factors including the specific active agent chosen and the benefit to be achieved, generally, an amount of from about 0.01% to about 10% by weight of the total composition may be suitable. Non-limiting examples of suitable active ingredients include enzymes such as thrombin that converts fibrinogen to fibrin, vasoconstrictors such as epinephrine, norepinephrine, angiotensin, or vasopressin, chemotherapeutic agents such as fluorouracil (5-FU), antimicrobials, antibiotics, and combinations of these active agents.

The pH of the compositions can be adjusted to from about 4 to 8. Agents suitable for adjusting the pH of the aqueous phase include, but are not limited to, buffering salts such as $NaH_2PO_4$, $NaHPO_4$, $KH_2PO_4$, $K_2HPO_4$, $NaHCO_3$, and $Na_2CO_3$, as well as mineral acids and bases such as hydrochloric acid and sodium hydroxide. The pH adjustment agents may be present in an amount of from about 0.01 to about 5% by weight of the total composition. In embodiments, the pH adjustment agent may be present in an amount of from about 0.1 to about 1% by weight of the total composition.

Thermally responsive polymers may provide the ability to deliver or inject a liquid, gel-on-contact material to the submucosa of one or more polyps to promote both the diagnosis and removal thereof. As used herein, a gel refers to a semisolid or semi-rigid system including a network of solid aggregates in which liquid is held.

In embodiments, compositions introduced into the submucosa and/or polyps may be shear thinning and show a decrease in viscosity with increasing rate of shear. Such shear thinning embodiments may be suitable for injection into the submucosa of one or more polyps in a highly viscosity state such as a gel at pre-treatment temperatures. The application of highly viscous shear thinning compositions provide the benefit of reducing and/or eliminating time needed for low viscosity compositions to become highly viscous upon warming. In embodiments, highly viscous shear thinning compositions may at the pretreatment temperature become even more viscous at the treatment temperature.

Polyps requiring removal may be pre-treated with compositions including a solvent and one or more polymers such as thermoreversible polymers and/or thermally responsive viscosity modifiers. These compositions are in a low viscosity state at a pre-treatment temperature and a higher viscosity or gel state at a treatment temperature that is higher than the pre-treatment temperature. In some embodiments additives may be included in the compositions of the present disclosure to further adjust the temperature at which the composition forms a gel.

Preconditioning polyps by injecting these compositions into the submucosa of one or more polyps may enhance the benefits of polypectomy, for example, by raising the polyps with a composition that gels or becomes more viscous when heated or applied to a patient's warm body, and/or does not readily escape polyps after initial incision thereof. Such preconditioning further improves the presentation of a polyp making it easier to grab and/or snare during excision.

In addition, treatment regimens in accordance with the present disclosure may improve a passage blocked by one or more polyps, and/or facilitate the removal of tissue having a propensity to develop into a cancerous lesion. Compositions utilized to raise polyps from the mucosal surface, at a pretreatment temperature and in a low viscosity state prior to being injected, may be injected into the submucosa of one or more polyps and allowed to warm to the treatment temperature such that the compositions increase in viscosity to a higher viscosity state such as a gel. In embodiments, the viscosity of these compositions at the treatment temperature may be higher then the viscosity of the compositions at the pre-treatment temperature. Treatment may then continue by removing the one or more polyps while the more viscous compositions in accordance with the present disclosure remain substantially in the submucosa and to some extent in the polyp.

Figure 1B:
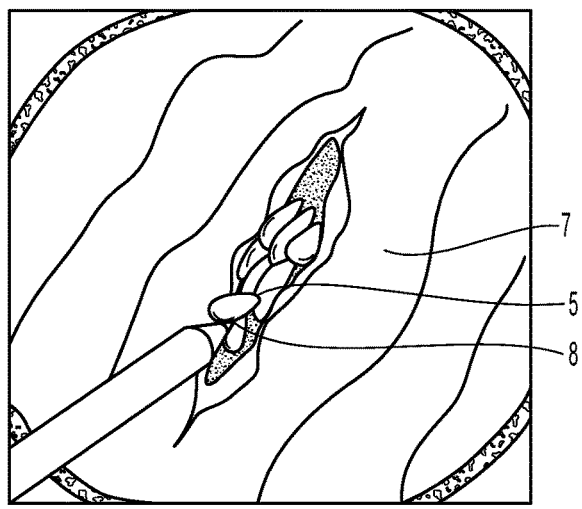
FIG. 1B is a is a schematic illustrations of the sessile villous adenoma of FIG. 1A which is injected submucosally with a composition in accordance with the present disclosure to elevate the lesion away from the colonic wall.
Figure 1C:
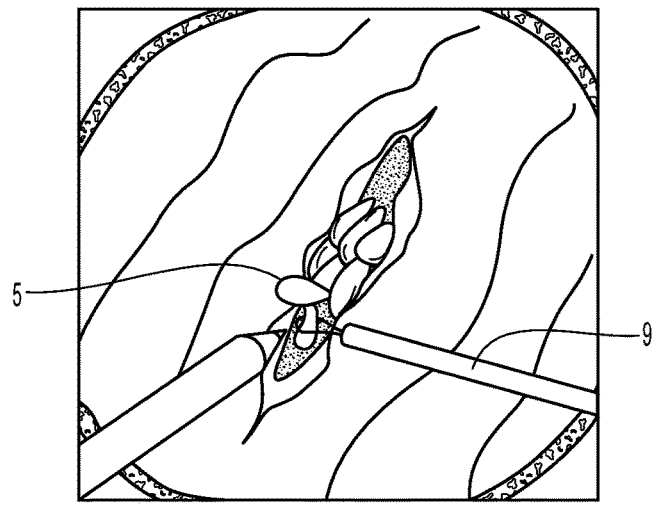
FIG. 1C is a schematic illustration of the sessile villous adenoma of FIG. 1A which can be removed piecemeal with a snare.
Figure 1D:
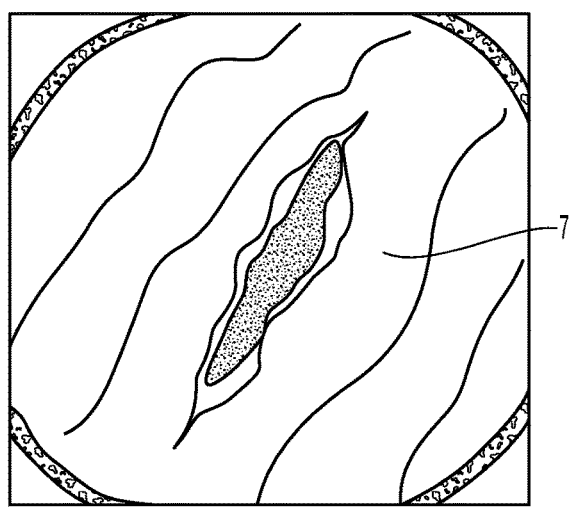
FIG. 1D is a schematic illustrations of the sessile villous adenoma of FIG. 1A at completion of a polyp resection.

Referring now to FIG. 1A, a schematic illustration shows a sessile villous adenoma polyp 5 on colonic wall 7 near the cecum of a 65 year old man. Sessile polyp 5 is substantially flat. Referring now to FIG. 1B, polyp 5 is injected submucosally with a composition in accordance with the present disclosure to elevate the lesion away from the colonic wall 7. Here, an aqueous composition including about 10% to about 50% by weight of one or more thermally responsive viscosity modifiers and water is injected into polyp 5 through needle 8. The composition is in a low viscosity state at a pre-treatment temperature and a higher viscosity state at a treatment temperature that is higher than the pre-treatment temperature. When the composition is warmed to the treatment temperature it increases in viscosity to the higher viscosity state. The viscosity of the composition at the treatment temperature may be at least about 2 times the viscosity of the composition at the pre-treatment temperature. In embodiments, the viscosity of the composition at the treatment temperature may be at least about 200 times the viscosity of the composition at the pre-treatment temperature. In embodiments, the viscosity of the composition at the treatment temperature may be from about 2 to about 80,000 times the viscosity of the composition at the pre-treatment temperature.

Where the composition is a highly viscous shear thinning composition, the shear thinning behavior of the composition allows for highly viscous compounds to be injected through needle 8. Referring now to FIG. 1C, sessile polyp 5 is shown schematically being removed piecemeal with a snare 9. As portions of polyp 5 are torn away from the polyp, the composition does not escape polyp 5 and the remaining portions of polyp 5 remain enlarged. FIG. 1D is a schematic illustrations of the sessile villous adenoma of FIG. 1A at completion of the polyp resection. The polyp is completely removed from colonic wall 7.

In embodiments, once a media has been injected into a polyp, one may then evaluate a polyp in situ to determine whether the polyp is cancerous or benign prior to removal. For example, one may evaluate a polyp's response to palpation with pressure or force sensors, or surface geometry scanning devices, such as laser scanning systems. Such systems could be used to determine the amount of pressure under the polyp (due to the injection of fluid) as well as responses to palpation. This response to pressure and/or palpation, as noted above, may be utilized to preliminarily diagnose the cancerous nature of a polyp. For example, a cancerous polyp may be more rigid and rise from the mucosal wall to a lesser degree compared with a benign polyp.

Any other method within the purview of one skilled in the art may be utilized to diagnose the cancerous nature of polyps in situ. Such methods include, but are not limited to, white light endoscopy, auto-fluorescent endoscopy, chromo endoscopy, narrow band imaging, immunophotodiagnostic endoscopy, optical coherence tomography, confocal fluorescence/reflectance micro-endoscopy (endomicroscopy), raman point spectroscopy, light scattering spectroscopy, fluorescent endoscopy, fluorescent imaging of quantum dots, combinations thereof, and the like.

Similarly, one could utilize air puffs to evaluate polyp biomechanics. For example, puffs of air are currently used to determine intraocular pressure. In a similar fashion, a puff of air could be directed at a polyp. As the pressure under the polyp (due to the injection of fluid) and the pressure in the air puff are known, one can evaluate geometric and mechanical properties of the polyp which may yield diagnostic information. Air-puff tonometers, which are capable of delivering such puffs of air, may also include sensors capable of detecting and analyzing the pressure differences between the air and the fluid below the polyp. Suitable tonometers include, for example, the TONO-PEN® XL applanation tonometer, the ATP Auto Non Contact Tonometer/Pachymeter, the AT555 Auto Non-Contact Tonometer, and similar tonometers, all commercially available from Reichert, Inc.

In embodiments, an air tonometer may include a nozzle for blowing air onto a polyp; a sensor capable of measuring the pressure of fluid injected below the mucosal layer, which is also below the polyp; and a CPU, optionally in combination with a display device, for comparing the pressure of air directed at the polyp with the pressure of the fluid under the polyp and providing the results of this comparison to a user. In embodiments, an air tonometer useful herein may also include an image pickup device for photographing an image of the polyp and memory for storing the image of the polyp, so that the optional display screen can display the image of the polyp stored both before and after administration of the puff of air. Again, these methods may permit the preliminary diagnose of a polyp in situ as described above.

Figure 2:
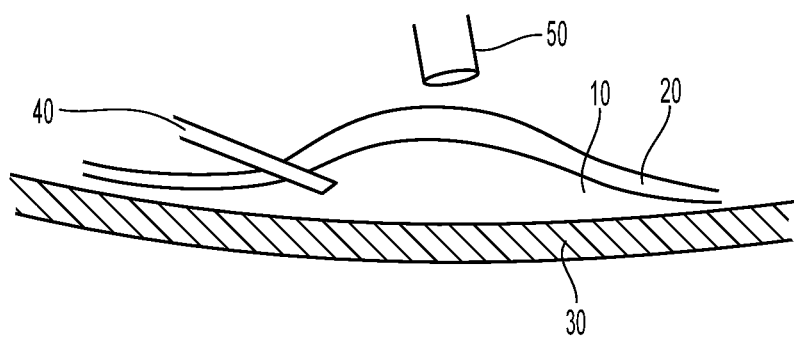
FIG. 2 is a depiction of a system which may be utilized to determine the cancerous nature of polyps in accordance with the present disclosure.

An example of the how the methods of the present disclosure could be carried out is depicted in FIG. 2. As set forth in FIG. 2, a media 10 such as saline may be injected under the mucosal layer 20 of colon wall 30 to raise the mucosal layer and permit analysis of the surface of mucosal layer 20, as well as any polyps thereon. The media 10 may be introduced by way of an injection cannula 40 or similar device, which may also possess a pressure sensor as described above so that the pressure under the polyp due to the injection fluid, in this case saline, may be monitored. Sensor 50 may then be positioned over the raised area of tissue and the biomechanics of the polyps may be evaluated. As noted above, suitable sensors which may be utilized as sensor 50 include, but are not limited to, pressure sensors, force sensors, cameras, surface geometry scanning devices such as laser scanning systems, tonometers as described above, white light endoscopes, auto-fluorescent endoscopes, chromo endoscopes, narrow band imaging devices, immunophotodiagnostic endoscopes, optical coherence tomography systems, confocal fluorescence/reflectance micro-endoscopes (endomicroscopy), raman point spectroscopes, light scattering spectroscopes, fluorescent endoscopes, fluorescent imaging of quantum dot systems, combinations thereof, and the like.

In other embodiments, a light source may be inserted under the polyp and saline injected therein followed by observation of any changes on the polyp surface under visible light, near infrared (which will display blood vessels), or other suitable light frequencies, including ultraviolet, and combinations thereof. In some embodiments a camera or similar device may be positioned above the polyp to visualize the polyp surface. In other embodiments a camera may be introduced underneath the polyp with the light source to permit visualization of the polyp as it separates from the colon wall from below the polyp.

Figure 3:
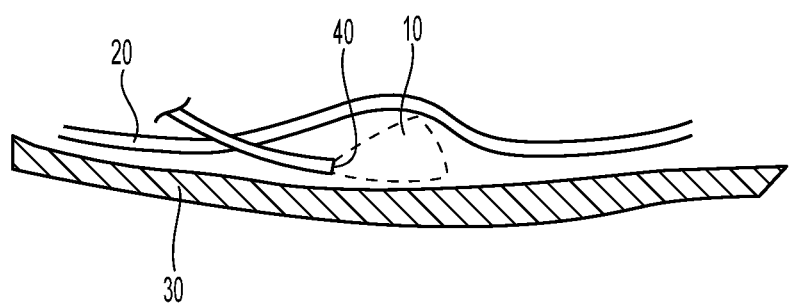
FIG. 3 is a depiction of an alternative system which may be utilized to determine the cancerous nature of polyps in accordance with the present disclosure.

An example of the how these methods could be carried out is depicted in FIG. 3. As set forth in FIG. 3, media 10 such as saline may be injected under the mucosal layer 20 of colon wall 30 to raise the mucosal layer and permit analysis of the surface of mucosal layer 20, as well as any polyps thereon. The media 10 may be introduced by way of an injection cannula 40 or similar device, which may also possess a light source or camera as described above (not shown), which may permit visualization of the polyp from below the polyp as it separates from the colon wall.

In accordance with the present disclosure, any delivery device within the purview of those skilled in the art may be utilized to introduce media into a polyp, for example saline or thermally responsive polymers as described above, as well as the sensors, cameras, and the like utilized to visualize the polyp during a polypectomy procedure. In embodiments, a multi-lumen cannula may be utilized.

The lumens may house and permit the transit of any suitable items and/or devices including, but not limited to, one or more medicines, drugs, blood, medical devices, guide wires, snares suitable for use in polypectomy procedures, electrocautery devices, needles, optical fibers, fiber optic imaging devices, fiber optic diagnostic probes, combinations thereof, and the like.

In embodiments, a suitable multi-lumen cannula may be a double lumen cannula. A double lumen cannula may possess any configuration within the purview of those skilled in the art. For example, in some embodiments, a single tube with a horizontal division of the tube which places the lumens of the cannula in immediate juxtaposition may be utilized.

In other embodiments, a coaxial double lumen cannula may be utilized. Such a cannula may possess concentric lumens, disposed one within the other.

A cannula in accordance with the present disclosure may be of any suitable length; in embodiments from about 1 meter to about 2.5 meters long, in other embodiments from about 1.25 meters to about 2.3 meters long.

A cannula may be introduced into a patient's body through a conventional colonoscope. While a cannula of the present disclosure may be constructed of any material within the purview of those skilled in the art, in embodiments a cannula of the present disclosure may be constructed of a comparatively soft medical grade plastic or metals such as stainless steel, titanium, and the like. Specific synthetic materials which may be utilized include, but are not limited to, fluoropolymers including polytetrafluoroethylene, polyurethane, polyethylene, polypropylene, high density polyethylene, nylons, polyethylene terephthalate, silicones, combinations thereof, and the like.

In embodiments, a needle may be attached to an end of one lumen of a cannula to facilitate introduction of media such as saline, thermally responsive polymers, and the like, into the mucosal wall or into a polyp during a polypectomy.

As noted above, in embodiments the cannulas may be utilized to introduce a composition for use in endoscopic polypectomy. The compositions may be applied to the submucosa of one or more polyps to improve presentation of the polyp and permit diagnosis as described above utilizing the methods of the present disclosure, and also make the polyp easier to capture with an endoscopic instrument such as a snare. For example, compositions having one or more thermoreversible and/or thermally responsive polymers may be injected into the submucosa of a polyp to improve its presentation.

The various constituents of compositions utilized to raise a polyp from the mucosal surface in accordance with the present disclosure may be combined with numerous ingredients to form products to be applied to the polyp, or other tissues of humans or other mammals. Such products may include a pharmaceutically acceptable carrier or diluent, vehicle or medium, for example, a carrier, vehicle or medium that is compatible with the tissues to which they will be applied. The term "dermatologically or pharmaceutically acceptable," as used herein, means that the compositions or constituents thereof are suitable for use in contact with tissues or for use in patients in general without undue toxicity, incompatibility, instability, allergic response, and the like.

Such active ingredients and formulations can be injected into the submucosa of a polyp in amounts sufficient to treat the affected area. As used herein the word "treat," "treating" or "treatment" refers to using the active ingredients and/or compositions prophylactically to prevent outbreaks of any undesirable conditions, or therapeutically to ameliorate an existing undesirable condition. A number of different treatments are now possible, which reduce and/or eliminate undesirable conditions.

As used herein "undesirable condition" refers to any detectable tissue manifestations caused by a polyp or removal thereof. Such manifestations can appear due to a number of factors such as, for example, trauma and/or other diseased or dysfunctional state. Non-limiting examples of such manifestations include the development of bleeding, cancer, inflammation, flakiness and/or other forms of tissue abnormality, and combinations thereof. It is understood, that the listed undesirable conditions are non-limiting and that only a portion of the conditions suitable for treatment in accordance with the present disclosure are listed herein.

In embodiments, compositions introduced into the submucosa of a polyp and/or a polyp may contain one or more active ingredients in an effective amount to improve undesirable conditions. As used herein "effective amount" refers to an amount of a compound or composition having active ingredients such as enzymes such as thrombin, vasoconstrictors such as epinephrine, norepinephrine, angiotensin, or vasopressin, chemotherapeutic agents such as fluorouracil (5-FU), and combinations of these active agents in amounts sufficient to induce a particular positive benefit to the polyp or tissue adjacent thereto. The positive benefit can be health-related. In embodiments, the positive benefit is achieved by contacting tissue with a coagulation protein to promote clotting and closure of the excised tissue. In embodiments, the positive benefit is achieved by contacting tissue with a vasoconstrictor to reduce bleeding. In embodiments, the positive benefit is achieved by contacting tissue with a chemotherapeutic agent to kill cancerous cells.

In order that those skilled in the art may be better able to practice the compositions and methods described herein, the following examples are given as an illustration of the preparation of the present compositions and methods of use thereof. It should be noted that the disclosure is not limited to the specific details embodied in the examples.

EXAMPLES 1-25

Non-limiting examples of compositions suitable for use in accordance with the present disclosure were formulated having the following constituents and characteristics set forth below in Table 1.

About 5 ml of samples of Examples 1-25 were subjected to a tilt test. Briefly, the tilt test involved placing about 5 ml samples in a test tube, placing the tubes in a temperature bath, and increasing the temperature in about 1° C. increments and holding the tube at that temperature for about 1 minute prior to tilting. For tilting, the tube was removed from the bath and tilted to about 90 degrees from vertical to see if there was any movement in the contents of the tube. The temperature at which the meniscus showed no movement was recorded as the gel temperature (sometimes referred to as the gel temp). Details of these Examples and their contents, as well as the results of the tests are set forth below in Table 1.

TABLE 1

| Example #* | PLURONIC F-127 Conc. % | PLURONIC F-68 Conc. % | Total Conc. % | Physical State at 25° C. | Gel Temp (tilt test) | DSC Transition Temp ° C. |
|---|---|---|---|---|---|---|
| 1 | 0 | 20 | 20 | liquid | >65 | 51.07 |
| 2 | 0 | 25 | 25 | liquid | >65 | 48.79 |
| 3 | 0 | 30 | 30 | liquid | >65 | 34.42 |
| 4 | 0 | 35 | 35 | liquid | 52 | 29.64 |
| 5 | 5 | 15 | 20 | liquid | >65 | 23.47 |
| 6 | 5 | 20 | 25 | liquid | >65 | 22.53 |
| 7 | 5 | 25 | 30 | liquid | 65 | 20.95 |
| 8 | 5 | 30 | 35 | liquid | 54 | 40.43 |
| 9 | 10 | 10 | 20 | liquid | >65 | 22.95 |
| 10 | 10 | 15 | 25 | liquid | >65 | 20.01 |
| 11 | 10 | 20 | 30 | liquid | 59 | 15.19 |
| 12 | 10 | 25 | 35 | liquid | 54 | 7.04 |
| 13 | 15 | 5 | 20 | liquid | 50 | 24.01 |
| 14 | 15 | 10 | 25 | liquid | 47 | 21.01 |
| 15 | 15 | 15 | 30 | liquid | 46 | 15.6 |
| 16 | 15 | 20 | 35 | liquid | 41 | 10.4 |
| 17** | 20 | 0 | 20 | gel | 24 | 22.2 |
| 18 | 20 | 5 | 25 | liquid | 31 | 19.7 |
| 19 | 20 | 10 | 30 | liquid | 33 | 15.51 |
| 20 | 20 | 15 | 35 | liquid | 31 | 10.47 |
| 21** | 25 | 0 | 25 | gel | <22 | 19.57 |
| 22** | 25 | 5 | 30 | gel | <23 | 16.58 |
| 23** | 25 | 10 | 35 | gel | <24 | 10.24 |
| 24** | 30 | 0 | 30 | gel | <25 | 13.86 |
| 25** | 30 | 5 | 35 | gel | <26 | 10.42 |

*Each example included solvent in the amount of from about 65% to about 80% by weight.
**Shear thinning embodiment.

EXAMPLE 26

Of the samples described in Examples 1-25 above, Example 18 and Example 16 were subjected to additional testing which included the addition of additives.

About 10 ml samples of Example 18 were individually combined with separate hydrophilic additives. The gel temperature for these samples was determined using the tilt test as described above.

The first additive was about 99.61 mg of a polyethylene glycol having a molecular weight of about 8000 (PEG 8000); this sample had a gel temperature of about 34° C. The second additive was about 104.7 mg of a polyethylene glycol having a molecular weight of about 10000 (PEG 10000); this sample had a gel temperature of about 34° C. The third additive was about 140 mg of sodium octyl sulfate; this sample had a gel temperature of about 38° C. The fourth additive was about 108 mg of sodium octyl sulfate; this sample had a gel temperature of about 35° C. The fifth additive was about 40 mg of sodium decyl sulfate; this sample had a gel temperature of about 29° C. The sixth additive was about 105 mg of sodium decyl sulfate; this sample had a gel temperature of about 45° C. An additional 10 ml sample without any additives was utilized as a control; this sample had a gel temperature of about 31° C.

Two 10 ml samples of Example 16 were individually combined with two separate additives. The gel temperature for these samples was determined using the tilt test as described above. The first additive was about 101.48 mg of NaCl; this sample had a gel temperature of about 36° C. The second additive was about 95 mg of SURFYNOL® MD-20, a non-silicone solvent-free liquid defoamer from Air Products and Chemicals, Inc. (Allentown, Pa.); this sample had a gel temperature of about 34° C. An additional 10 ml sample without any additives was utilized as a control; this sample had a gel temperature of about 41° C.

Example 18 and Example 13 were combined with the various additives and the effect on gel temperature was determined using the tilt test described above. The sample and additives added thereto, as well as the gel temperature observed (Gel Temp) are set forth below in Tables 2 and 3 (Table 2 is for the samples prepared with Example 18 and Table 3 is for the samples prepared with Example 13). Additional additives included sodium octyl sulfate; sodium decyl sulfate; NaCl, TRITON® 100 and TRITON® 114 (nonionic surfactants from Sigma-Aldrich); SPAN 65 (a sorbitan tristearate surfactant), SPAN 80 (a sorbitan monooleate surfactant) and SPAN 85 (a sorbitan trioleate surfactant); TWEEN 60 (a monostearate surfactant); and SURFYNOL® MD-20.

TABLE 2

| Sample # (Example 18: 20% F127 + 5% F68) | mg | additive | Additive conc. % wt | Gel Temp ° C. |
|---|---|---|---|---|
| 1a | 0 | control | 0.00 | 31 |
| 2a | 20 | Octyl* | 0.20 | 30 |
| 3a | 50 | Octyl | 0.50 | 30 |
| 4a | 100 | Octyl | 0.99 | 33 |
| 5a | 150 | Octyl | 1.48 | 36 |
| 6a | 200 | Octyl | 1.96 | 43 |
| 7a | 20 | Decyl** | 0.20 | 29 |
| 8a | 50 | Decyl | 0.50 | 30 |
| 9a | 100 | Decyl | 0.99 | 39 |
| 10a | 150 | Decyl | 1.48 | 58 |
| 11a | 200 | Decyl | 1.96 | >60 |
| 12a | 100 | TRITON 100 | 0.99 | 29 |
| 13a | 100 | TRITON 114 | 0.99 | 28 |
| 14a | 100 | TWEEN 60 | 0.99 | 29 |
| 15a | 100 | SPAN 65 | 0.99 | 30 |
| 16a | 100 | SPAN 80 | 0.99 | 34 |
| 17a | 100 | SPAN 85 | 0.99 | 30 |
| 18a | 100 | NaCl | 0.99 | 26 |

*n-Sodium Octyl Sulfate
**n-Sodium Decyl Sulfate

TABLE 3

| Sample # (Example 13: 15% F127 + 5% F68) | mg | additive | Additive conc. % wt | Gel Temp ° C. |
|---|---|---|---|---|
| 1b | 0 | control | 0.00 | 50 |
| 2b | 20 | NaCl | 0.20 | 49 |
| 3b | 50 | NaCl | 0.50 | 47 |
| 4b | 100 | NaCl | 0.99 | 45 |
| 5b | 150 | NaCl | 1.48 | 44 |
| 6b | 200 | NaCl | 1.96 | 41 |
| 7b | 20 | SPAN 85 | 0.20 | 49 |
| 8b | 50 | SPAN 85 | 0.50 | 49 |
| 9b | 100 | SPAN 85 | 0.99 | 49 |
| 10b | 150 | SPAN 85 | 1.48 | 49 |
| 11b | 200 | SPAN 85 | 1.96 | 49 |
| 12b | 100 | TRITON 100 | 0.99 | 43 |
| 13b | 100 | TRITON 114 | 0.99 | 42 |
| 14b | 100 | TWEEN 60 | 0.99 | 47 |
| 15b | 100 | SPAN 65 | 0.99 | 49 |
| 16b | 100 | SPAN 80 | 0.99 | 54 |
| 17b | 100 | SURFYNOL MD-20 | 0.99 | 46 |

In addition, about 250 mg of NaCl was added to an additional sample of Example 13; the resulting material had a gel temperature of about 39° C. Also, about 300 mg of NaCl was added to an additional sample of Example 13; the resulting material had a gel temperature of about 38° C.

Figure 4A:
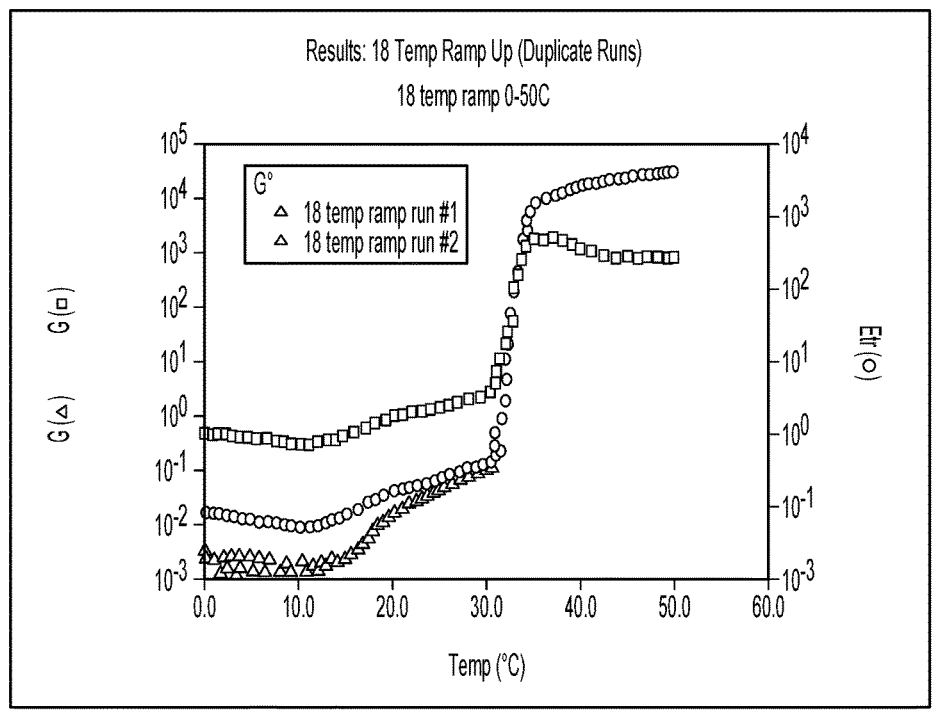
FIGS. 4A, 4B, 4C and 4D are graphs depicting the rheology of samples of compositions of the present disclosure as the samples were subjected to increasing temperature.
Figure 4B:
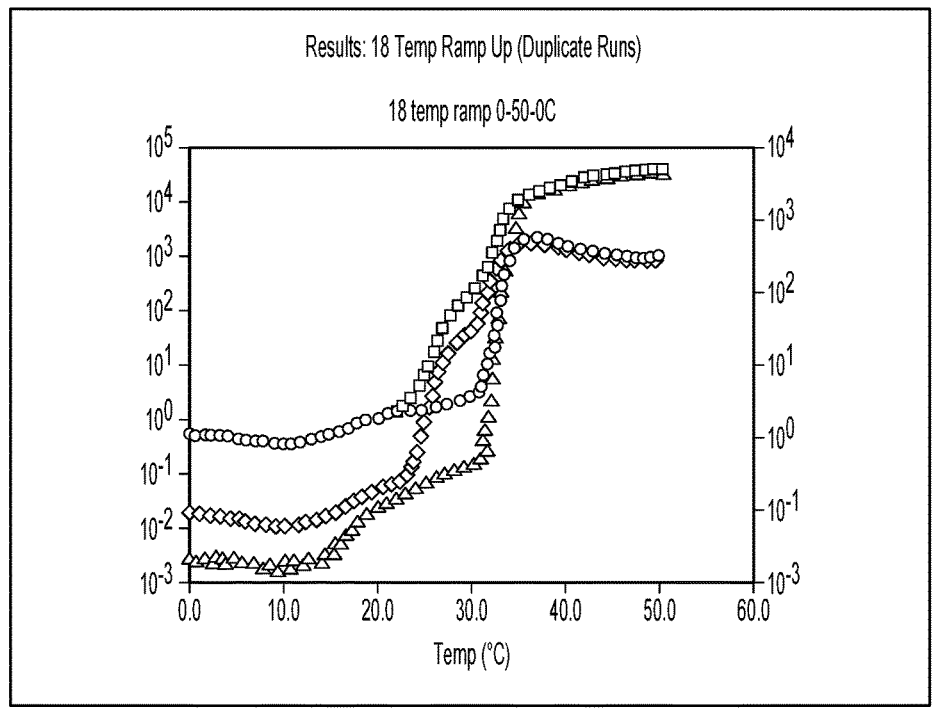
Figure 4C:
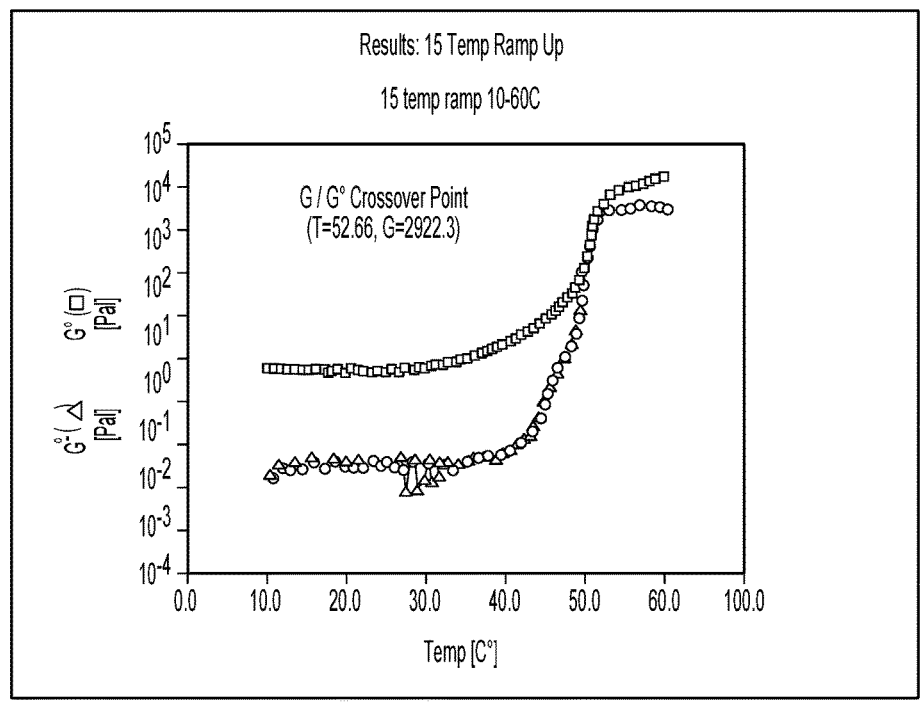
Figure 4D:
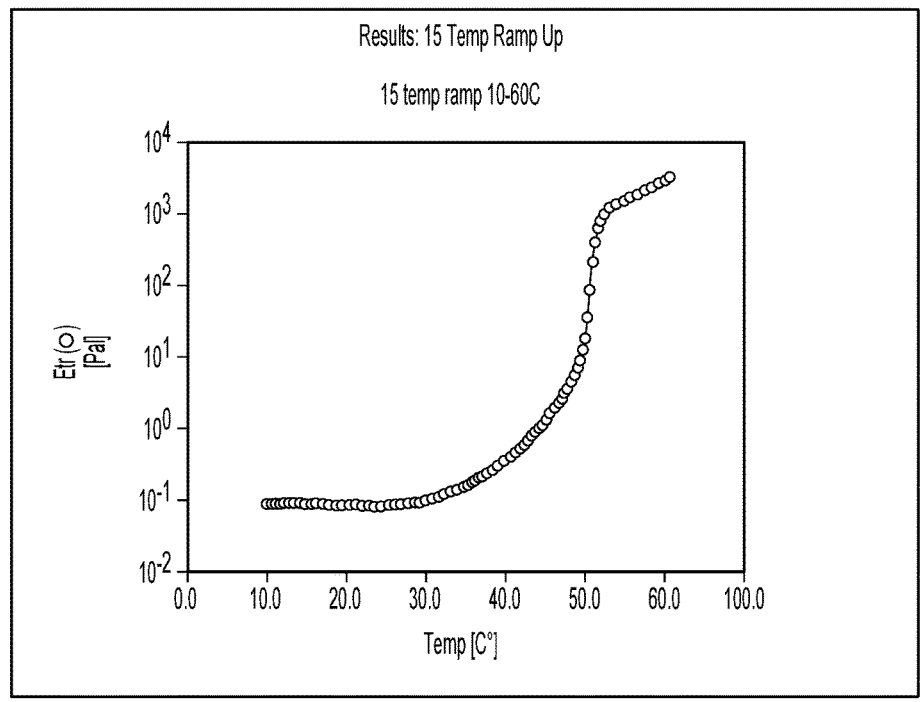
Figure 5A:
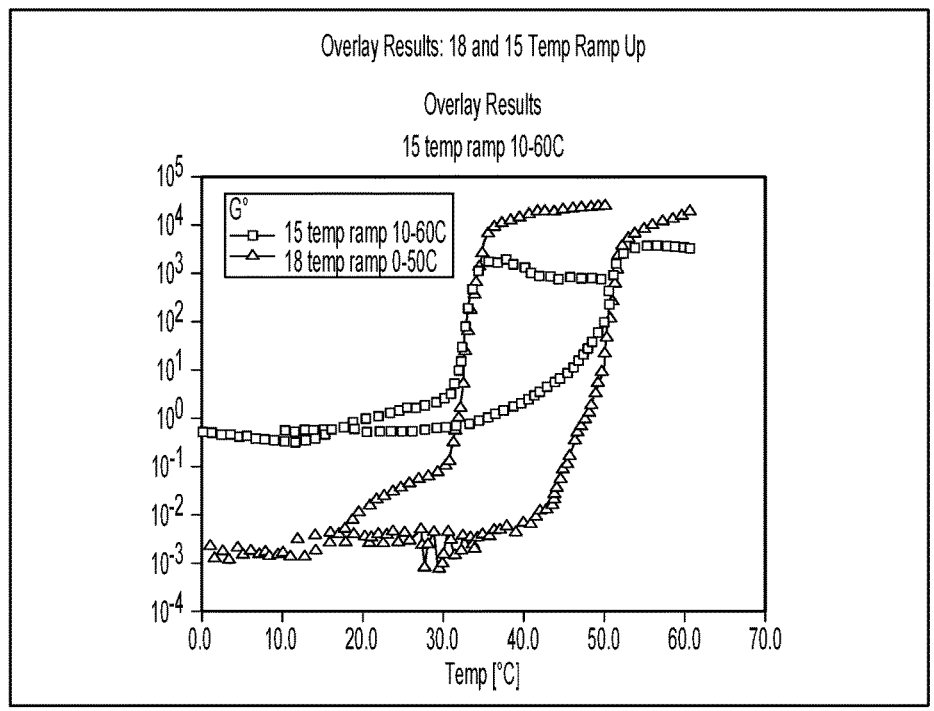
FIGS. 5A, 5B, 5C and 5D are graphs depicting the rheology of additional samples of compositions of the present disclosure as the samples were subjected to increasing temperature.
Figure 5B:
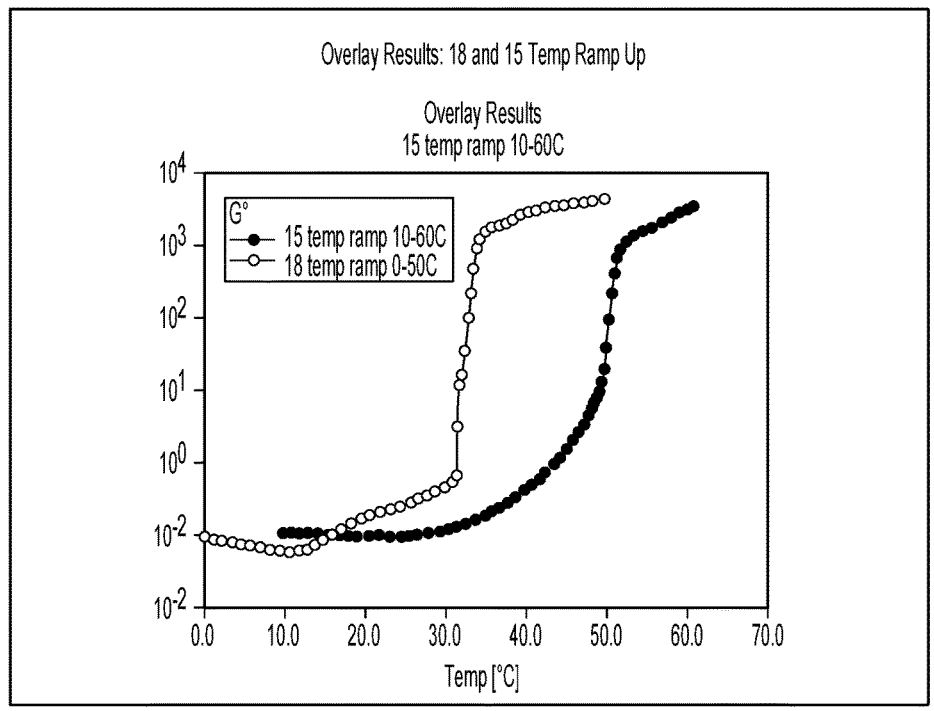

Samples of Examples 18 and 15 were subjected to rheology testing by measuring their viscosity with an increase in temperature. The system utilized for this rheology testing was an ARES LS2 rheometer with Peltier temperature control system from TA Instruments. The ARES uses a 50 mm parallel plate with a solvent trap. A dynamic temperature ramp from 0 to 60° C. or 10 to 60° C. was selected with a 1° C./minute ramp rate and 6.28 rad/s frequency. The strain was within the linear viscoelastic region with auto strain and auto tension both active during the tests. Elastic and storage moduli along with viscosity were all plotted as a function of temperature. FIGS. 4A and 4B depict the results of this testing for Example 18; FIGS. 4C and 4D depict the results of this testing for Example 15. Graphs depicting an overlay of the results obtained for Examples 18 and 15 are set forth as FIGS. 5A and 5B.

Figure 6A:
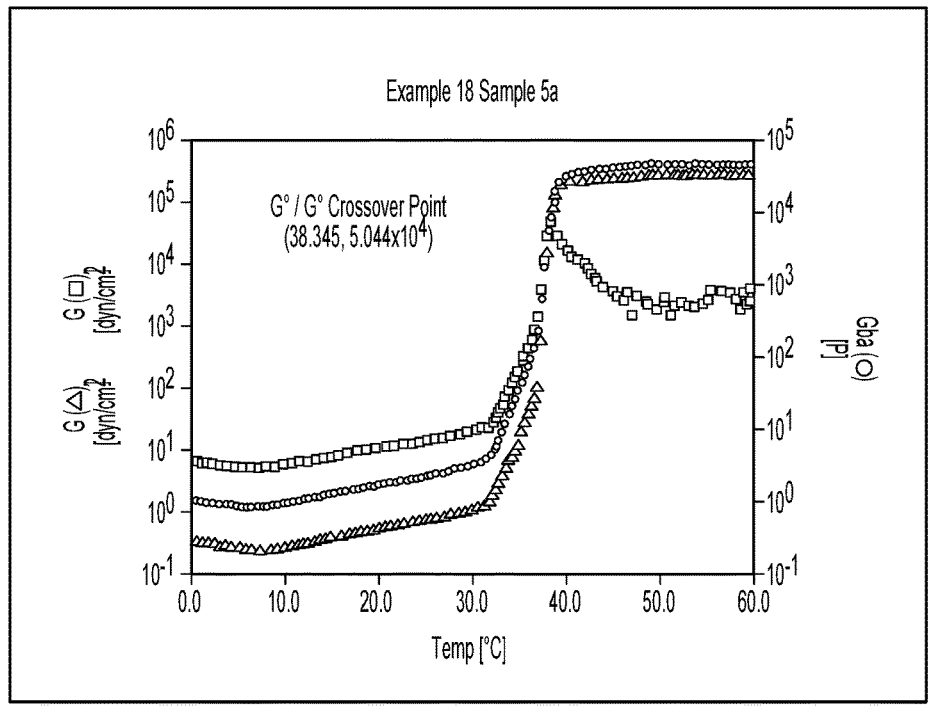
FIGS. 6A and 6B are graphs depicting the rheology of additional samples of compositions of the present disclosure as the samples were subjected to increasing temperature.
Figure 6B:
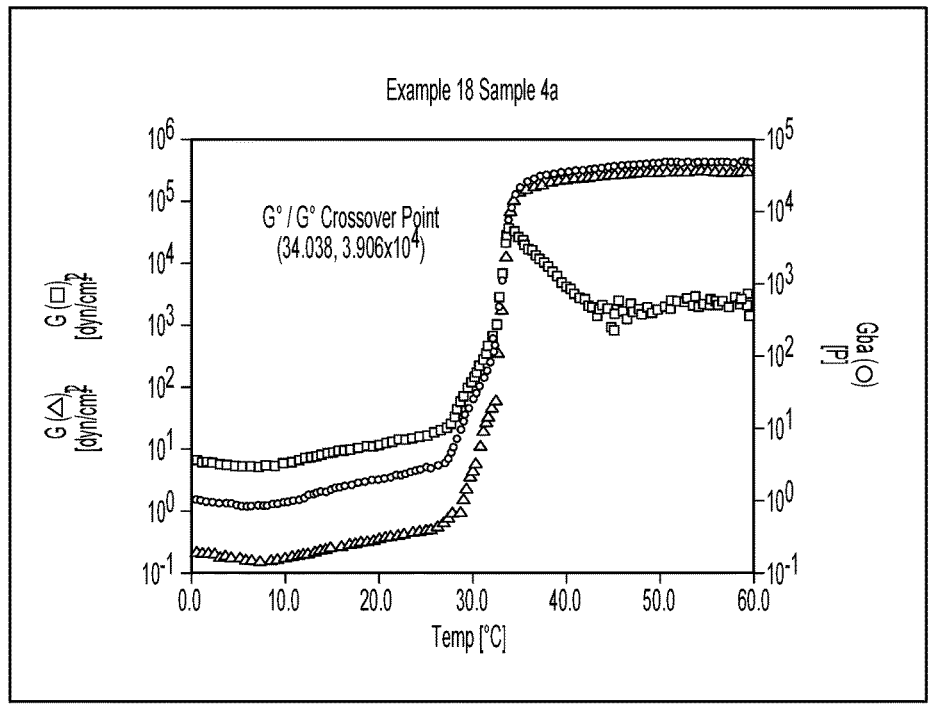

Samples of Example 18 with additives, specifically samples 5a and 4a from Table 2 above, were also subjected to this rheology testing. Graphs depicting the results obtained for these samples are set forth as FIGS. 6A and 6B, respectively.

EXAMPLE 27

Figure 5C:
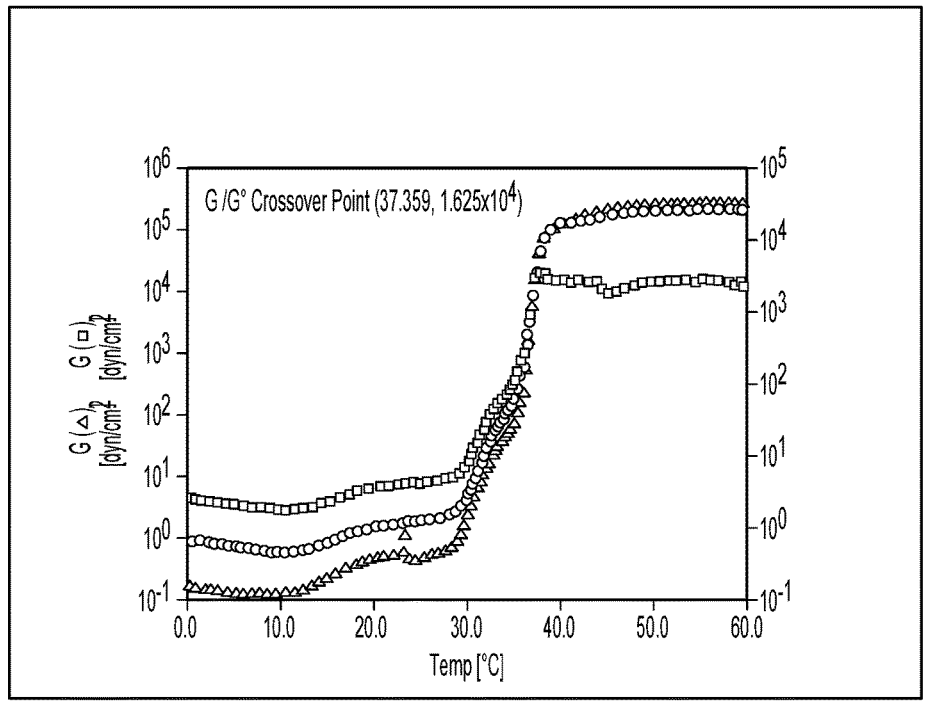
Figure 5D:
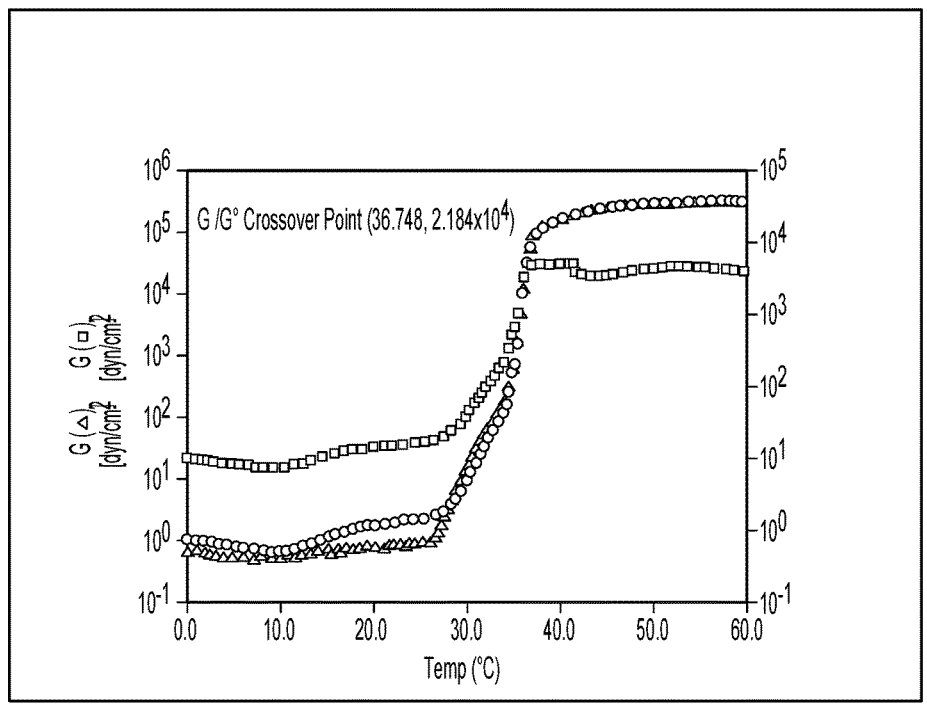

Another sample was prepared using about 18% by weight of PLURONIC F-127 and about 5% by weight of PLURONIC F-68. The gel temperature of this material without any additives was from about 36° C. to about 37° C. Upon the addition of about 50 mg NaCl, the gel temperature was about 35° C.; upon the addition of about 100 mg of NaCl, the gel temperature was about 33° C. This sample was subjected to rheology testing as described above in Example 26. A graph depicting the results of the testing on the sample without additives is provided as FIG. 5C; a graph depicting the results of the testing on the sample with 100 mg NaCl is provided as FIG. 5D.

EXAMPLE 28

A composition of Example 27 without any additives is prepared by, inter alia, combining about 18% by weight poloxamer (PLURONIC F-127) with about 5% by weight poloxamer (PLURONIC F-68) into an aqueous solubilizing medium suitable for injection into a human. The composition is injected submucosally as a liquid into a sessile villous adenoma near the cecum of a 60 year old man. The liquid composition gels upon contact with the man's body heat. The sessile polyp is removed in a piece meal fashion using a snare. The gelled composition does not leak out of the polyp after the first, second, or third excision. Excision continues until the completion of the polyp resection.

EXAMPLE 29

A composition of Example 18 is prepared by, inter alia, combining about 20% by weight of a first poloxamer (PLURONIC F-127) with about 5% by weight of a second poloxamer (PLURONIC F-68) into an aqueous medium suitable for injection into a human. The composition is injected submucosally as a shear thinning gel into a pedunculated polyp near the cecum of a 65 year old man. The gel composition further thickens upon contact with the man's body heat. The polyp is removed in a piece meal fashion using a snare. The gelled shear thinning composition does not leak out of the polyp during the polyp resection.

EXAMPLE 30

A composition of Example 27 is prepared by, inter alia, combining about 18% by weight poloxamer (PLURONIC F-127) with about 5% by weight poloxamer (PLURONIC F-68) into an aqueous solubilizing medium suitable for injection into a human. The composition further includes about 2% by weight chemotherapeutic active agent fluorouracil (5-FU). The composition is injected submucosally as a liquid into a cancerous sessile villous adenoma near the cecum of a 68 year old man. The liquid composition gels upon contact with the man's body heat. The sessile polyp is removed in a piece meal fashion using a snare. The gelled composition does not leak out of the polyp after the first, second, or third excision. Excision continues until the completion of the polyp resection. No further revision procedure is needed.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method comprising: introducing at least one media comprising at least one thermally responsive polymer into tissue comprising submucosa of a polyp; measuring a response to an external stimuli in the tissue, the external stimuli being an air puff; and deducing a state of health of the tissue by measuring the response to the air puff with a tonometer.

2. The method of claim 1, wherein the media further comprises saline.

3. The method of claim 1, wherein the media comprises at least one thermoreversible polymer.

4. The method of claim 1, wherein deducing the state of health of the tissue comprises determining whether or not the polyp is cancerous.

5. The method of claim 1, wherein deducing the state of health of the tissue comprises deducing the state of health in real time.

* * * * *